United States Patent [19]

Zhang et al.

[11] Patent Number: 5,629,457
[45] Date of Patent: May 13, 1997

[54] DEPHENOLIZING PROCESS FOR PRODUCTION OF HIGH-QUALITY POLYCARBONATE GRADE BISPHENOL A

[75] Inventors: Minhua Zhang; Zongzhang Liu; Shenbo Yu; Shenghua Qian; Chuanzhao Li, all of Tianjin, China

[73] Assignees: Tianjin University, Tianjin; China Petro-Chemical Corporation, Beijing, both of China

[21] Appl. No.: 501,138

[22] PCT Filed: Feb. 16, 1994

[86] PCT No.: PCT/CN94/00014

§ 371 Date: Sep. 29, 1995

§ 102(e) Date: Sep. 29, 1995

[87] PCT Pub. No.: WO94/19303

PCT Pub. Date: Sep. 1, 1994

[30] Foreign Application Priority Data

Feb. 16, 1993 [CN] China ............... 93101414.X

[51] Int. Cl.$^6$ ............................................... C07C 37/68
[52] U.S. Cl. ............................................... 568/724
[58] Field of Search ............................................... 568/724

[56] References Cited

U.S. PATENT DOCUMENTS

| | | | |
|---|---|---|---|
| 4,590,303 | 5/1986 | Mendiratta | 568/728 |
| 4,740,634 | 4/1988 | Gomes de Matos et al. | 568/724 |
| 4,798,654 | 1/1989 | Iimuro et al. | 203/94 |
| 4,847,433 | 7/1989 | Kissinger | 568/727 |
| 4,954,661 | 9/1990 | Iimuro et al. | 568/727 |
| 5,105,026 | 4/1992 | Powell et al. | 568/727 |
| 5,198,591 | 3/1993 | Kiedik et al. | 568/727 |
| 5,210,329 | 5/1993 | Gomes de Matos et al. | 568/727 |
| 5,269,887 | 12/1993 | Jakob et al. | 568/724 X |
| 5,382,711 | 1/1995 | Asaoka et al. | 568/724 X |
| 5,399,784 | 3/1995 | Asaoka et al. | 568/724 X |
| 5,512,700 | 4/1996 | Patrascu et al. | 568/724 |
| 5,527,971 | 6/1996 | McKinnie | 568/724 X |

FOREIGN PATENT DOCUMENTS

| | | |
|---|---|---|
| 738962 | 9/1969 | Belgium . |
| 0332203B1 | 5/1993 | European Pat. Off. . |
| 3-284641 | 12/1991 | Japan . |

OTHER PUBLICATIONS

Japanese Abstract: 01-238550, Sep. 1989.
Japanese Abstract: 62-192331, Aug. 1987.

*Primary Examiner*—Paul F. Shaver
*Attorney, Agent, or Firm*—Chilton, Alix & Van Kirk

[57] ABSTRACT

A process for producing high-quality polycarbonate grade bisphenol A directly by removing phenol from the adduct crystal of bisphenol A with phenol via a gas-solid reaction at low temperature comprises directly feeding the adduct crystal into a vacuum or pneumatic dephenolizing device under vacuum a inert gas stream, controlling the temperature of the adduct crystal below its melting point, decomposing the adduct crystal into gas phase and solid phase, removing the gas phase phenol and condensing phenol for recovery, well leaving the rest being the desirable bisphenol A. The process possesses easy operation, short procedure, low energy consumption, and high purity and good color of bisphenol A obtained. Bisphenol A produced according to the process of the invention may be used as the raw material for producing polycarbonates for optical use.

11 Claims, No Drawings

DEPHENOLIZING PROCESS FOR PRODUCTION OF HIGH-QUALITY POLYCARBONATE GRADE BISPHENOL A

This applicant is a 371 of PCT/CN94/0014, filed Feb. 16, 1986.

TECHNICAL FIELD

The present invention relates to a new dephenolizing process for producing high-quality polycarbonate grade bisphenol A, especially to, in the reaction product of acetone with phenol, a process for directly obtaining high-purity bisphenol A with good color from the reacted adduct crystal via a gas-solid dephenolizing treatment at low temperature.

It is well known that bisphenol A is a major raw material for producing polycarbonates and epoxy resins, especially for polycarbonates. The wide use of the products from bisphenol A in optical articles in recent years causes a substantial increase in the demand for bisphenol A, in particular a rapid increase in the demand for colorless, high purity bisphenol A.

Generally, bisphenol A is commercially produced by reacting acetone with excess phenol in an acidic circumstance, using a modified cation exchange resin as catalyst, in order to obtain a reaction product containing bisphenol A, which contains, in addition to bisphenol A, unreacted acetone and phenol, formed water and other by-products. Therefore, a procedure of removing the impurities described above and purifying bisphenol A, such as concentration, crystallization, separation, as well as dephenolization, must be added to the procedure design to obtain bisphenol A.

BACKGROUND ART

Since the presence of the above impurities deteriorate the properties of the product resins prepared from bisphenol A, a close attention is paid for obtaining high-quality bisphenol A from the reaction product described above. Extensive researches have been done in order to obtain high-quality bisphenol A. A preferable process is that the condensation reaction liquor is fed into a crystallizer with a special construction after being concentrated by a concentration column, cooled to crystallize bisphenol A in the form of 1:1 (molar ratio) adduct crystal of bisphenol A with phenol, followed by centrifugal filtration and washing, to obtain the relatively pure adduct crystal, then bisphenol A is obtained by removing phenol from the adduct crystal.

In order to obtain high-purity bisphenol A by removing phenol from the adduct crystal of bisphenol A with phenol, researchers proposed various methods such as recrystallization, solvent extraction, distillation and steam stripping. For example, a recrystallization method by using water as solvent is disclosed in U.S. Pat. No. 4,212,997/1980 to General Electric Company. In this process, water of an amount of 8 to 10 times more than that of bisphenol A is added to the adduct, which is allowed to melt thoroughly at a temperature of 80°–90° C. The mixture is well stirred and cooled, and a prismatic crystal of bisphenol A is precipitated, which is filtered off with a purity up to 99.2% by weight, and a phenol content of less than 1% by weight. If a further purification is needed, water may be used or an organic solvent of bisphenol A insoluble or slightly soluble may be selected to wash the bisphenol A crystal. A method using methylene chloride as solvent is described in U.S. Pat. No. 4,156,098/1979 to the General Electric Company, wherein the adduct is dissolved at a temperature of no higher than 60° C., then the temperature is lowered to 30°–40° C., and a bisphenol A crystal of relatively crude size is formed. After filtration, the crystal is washed with methylene chloride of an amount of twice as much as that of the adduct to obtain a white crystal of bisphenol A with a purity of 99.24%. The large amount of water or solvent introduced by the recrystallization method brings about a need for the recovery of a substantial amount of water or solvent, thus considerably increase the capital cost and operation cost.

A dephenolizing method often used is decomposing the adduct by heating in vacuum and distilling phenol at the same time. For example, U.S. Pat. No. 3,936,507 discloses a process by vaporizing the adduct crystal at over 180° C. for 0.1–30 minutes under reduced pressure and obtaining bisphenol A by fractional condensation. In such a distillation process, bisphenol A is heated at high temperature and easy to decompose, which produces new impurities and colored substances, thus makes it difficult to secure the desired high-purity and color level of polycarbonate grade bisphenol A. In general, there is also a need for a further procedure of hot water recrystallization as described in U.S. Pat. No. 4,209,646 or solvent washing as described in U.S. Pat. No. 4,492,807. As is noted in EP 0,343,349, phenol can not be completely removed only by distillation, a further procedure is needed, such as steam stripping as described in JP 43937/1972 or solvent recrystallization as described in JP 88137/1982. Accordingly, not only the stock is subjected to high temperature by using the dephenolizing method of distillation, but there is also a problem of a large amount of solvent recovery caused by its further procedure, as well as problem for treatment of a large amount of phonetic waste water caused by steam stripping method. So the whole procedure of refining bisphenol A becomes longer, which causes a substantial increase of capital cost and operation cost. The purity of bisphenol A can be increased by increase the capital and operation cost in some methods, however, due to the colored impurities caused by high temperature operation, the color of the product is difficult to be assured.

Also a process is disclosed in TOKKOSHO 36-23335 of heating the adduct to a temperature above 50° C. in a solvent with a boiling point higher than 50° C. and extracting only the phenol portion from the adduct. It also presents the above mentioned problems of solvent recovery and loss of bisphenol A from solvent dissolution.

DISCLOSURE OF INVENTION

To sum up, in the process of removing phenol from the adduct crystal, it inevitably encounters the problems such as the defects of the yield and qualities (such as color) decrease of bisphenol A due to the high temperature or the increase of capital and operation cost of solvent recovery that is difficult to overcome, whether by recrystallization, distillation, or steam stripping method. There is also a serious problem of waste water treatment for steam stripping method.

In order to avoid heating the adduct crystal at high temperature, decrease the capital and operation cost, and obtain high-purity and good color bisphenol A product, the present inventors develop a bright new process of gas-solid dephenolization at low temperature.

The adduct of bisphenol A with phenol is an unstable adduct crystal, which tends to decompose when heated. Under the presence of vacuum or gas stream, below its melting point, the adduct crystal decomposes to bisphenol A solid and phenol gas, above its melting point, the adduct crystal melts. During the dryness of the adduct crystal, the present inventors unexpectedly discover that the decomposition pressure of the adduct crystal of bisphenol A with phenol is considerably greater than the saturated vapor pressures of liquid phenol and the mixture solution of phenol and bisphenol A, which demonstrates that the adduct crystal of bisphenol A with phenol can decompose at relatively low temperature and phenol can be removed. As is proven by experiment, bisphenol A is contacted with oxygen to worsen its color, the present inventors suggest a method of removing phenol under vacuum or by inert gas during the gas-solid reaction of removing phenol from the adduct crystal, in order to complete the invention of directly obtaining high-quality bisphenol A from the adduct crystal under low temperature condition.

An object of this invention is to provide a process for producing high-quality polycarbonate grade bisphenol A by removing phenol from the adduct crystal of bisphenol A with phenol, which uses neither solvents or water, or any high temperature procedure, but utilize the gas-solid reaction to remove phenol from the adduct crystal and directly obtain high-quality polycarbonate grade bisphenol A.

A further object of this invention is to provide a process for producing high-quality polycarbonate grade bisphenol A by removing phenol from the adduct crystal of bisphenol A with phenol, which comprises directly feeding the adduct crystal into a vacuum or pneumatic dephenolizing device under vacuum or inert gas stream, controlling the temperature of the adduct crystal below the melting point of the adduct crystal, decomposing the adduct crystal to a gas phase and a solid phase and, in which the gas phase phenol being removed from the dephenolizing device by vacuum or inert gas stream is condensed for recovery, and obtaining the high-quality polycarbonate grade bisphenol A directly from the dephenolizing device.

In the dephenolizing process of the present invention, the moisture content of the adduct crystal should be controlled below 30% by weight, preferably low moisture content. Said dephenolizing device is commercially available. There is no special desire for the dephenolizing device in this process. Under vacuum or inert gas stream condition, the stock can be at the static or fluidizing state. As operating medium, the inert gas comprises any gas which is unreactive to bisphenol A and phenol, as well as the adduct crystal thereof, such as nitrogen, argon. Therefore, a heat exchanger should be installed inside the dephenolizing device to supply the heat needed in the gas-solid dephenolizing reaction. The temperature of the adduct crystal is controlled between 40° and 130° C. The adduct crystal decomposes into two phases when heated, wherein bisphenol A forms the solid phase, and phenol forms the gas phase, the gas phase of phenol is removed from the dephenolizing device by vacuum or inert gas stream, thus high-purity bisphenol A is directly obtained. Both batch and continuous methods of operation can be used in the dephenolizing process of the invention. During the batch operation, the operating conditions of the vacuum dephenolizing device are as follows: the temperature is preferably risen from 60° to 130° C., the rising rate of temperature may be varied according to the corresponding residence time and is from 0.2°–2.0° C./min, and the preferred rate is 1.2° C./min; the operating pressure is 266.644–6,666.1 Pa(2–50 torr), and the residence time is 1–4 hrs. During the batch operation, the operating conditions of the pneumatic dephenolizing device are as follows: the temperature is preferably risen from 60° to 130° C., and the rising rate of temperature is from 0.2° to 2° C./min, and the preferred rising rate of temperature is 1.2° C./min, the residence time is 1–3.5 hrs, and the flow rate of the inert gas stream is 0.1–0.5 m/s. During the continuous operation, the operating temperature may be divided into at least two sections, for example, for the operation with three sections, the first is 60°–85° C., the second is 85°–110° C., and the third is 110°–130° C. The ratio of the operation times of the three sections is approximately 2:1:2, and the total residence time is 1–4 hrs.

Compared to those in the prior art, the process of the invention has the following distinct advantages:

1. It is not necessary for the adduct crystals to be dephenolized by distillation at high temperature, the operating temperature is far below the decomposition temperature of bisphenol A and no new impurities and colored substances formed, which assure the product bisphenol A with high purity and good color.

2. It is not necessary for the adduct crystal to be subjected to solvent extraction or recrystallization, thus the problem of a large amount of solvent recovery because of the dephenolization by solvent extraction or recrystallization is avoided. The procedure of the present invention is simplified, and the capital cost and operation cost are substantially decreased.

3. The per pass yield for preparing bisphenol A by decomposing the adduct crystal according to the process of the invention is almost 100%.

The indexes of the product bisphenol A obtained using the process of this invention are as follows:

purity>99.95% by weight melting point>156.8° C.

free phenol<100 ppm ash<0.01% by weight color APHA (50% alcohol)<10 iron content<0.1 ppm

BEST MODE FOR CARRYING OUT THE INVENTION

The following examples further illustrate the process of this invention but not limit the scope of the invention.

EXAMPLE 1

5 kg of the adduct crystal of bisphenol A with phenol with weight percent composition of 33.25 phenol, 66.73 bisphenol, 0.02 2,4-bisphenol A and traces of the others and with a moisture content of 4.7% by weight was added to the vacuum dephenolizing device. The vacuum dephenolizing device was a cylindrical vacuum desiccator with a electric heater installed inside and a condenser for condensing phenol outside, cooling water of 35° C. was passed through the condenser. The absolute pressure in the dephenolizing device was 1333.22 Pa(10 torr), the programmed temperature for the stock was from 60° C. to 130° C., the residence time was 1.5 hrs, during which the adduct crystal was subjected to heat and a gas-solid reaction took place with the adduct crystal, the gas phase phenol was condensed by a condenser for recovery. At the end of the operation, 3.34 kg of solid product bisphenol A was obtained, having a color of 6 APHA (50% alcohol solution), a phenol content of 25 ppm, and a purity of greater than 99.95% by weight, which was sufficient to meet the needs of the raw material for polycarbonates for optical use.

EXAMPLE 2

10 kg of the adduct crystal of the same composition as in example 1 was fed to the pneumatic dephenolizing device, which is a fluidizing reactor equipped with coil for heating and a jacket and with a condenser installed outside, recycling hot oil was passed through the coil and the jacket, cooling water of 35° C. was passed through the condenser. The gas for fluidizing was industrial grade nitrogen (99% by weight, purity), the flow rate of the gas stream 0.3 m/s, the residence time of the stock was 1 hr. The programmed temperature of the stock was from 50° to 125° C., during which the adduct crystal was subjected to heat and a gas-solid decomposition reaction took place, the gas phase phenol was carried away by the nitrogen stream and condensed by the condenser for recovery. At the end of operation, 6.67 kg of solid bisphenol A was obtained, having a color of 7 APHA (50% alcohol solution), a phenol content of 37 ppm, and a purity of 99.95% by weight, which was sufficient to meet the needs of the raw material for the polycarbonates for optical use.

EXAMPLE 3

According to the process of example 1, 5 kg of the adduct crystal was fed into the vacuum dephenolizing device. The adduct crystal was composed of 48.98% by weight of bisphenol A, 51.00% by weight of phenol, 0.02% by weight of 2, 4-bisphenol A, and traces of others. The operating pressure was 5332.88 Pa(40 torr), the programmed temperature of the stock was from 45° to 130° C., the residence time is 4 hrs. Other conditions were the same as that in example 1. At the end of the operation, 2.45 kg of solid bisphenol A was obtained, having a phenol content of 45 ppm, a color of 7 APHA (50% alcohol solution), and a purity of greater than 99.95% by weight, which was sufficient to meet the needs of the raw material for polycarbonates for optical use.

EXAMPLE 4

The adduct crystal of the same composition as in Example 1 was fed into a continuous vacuum drying apparatus at a rate of 10 Kg/hr. Two tanks by turn should be needed to finish the feeding of the vacuum drying apparatus, and the drawing is the same as above. A gas-catch tank and followed with vacuum system. The operating temperature in the drying apparatus is divided into three different sections, the first is 60°~85° C., the second is 85°~110° C. and the third is 110°~1° C., the ratio of the operation time of the three sections is 2:1:2. The heaters in the drying apparatus heat the three sections to the desired temperature. The operating pressure in the drying apparatus is 1333.22 Pa(10 torr)(abs.). The fed adduct crystal is moved from low to high temperature. During the moving, it is continuously decomposed into gas phase phenol and solid phase bisphenol A. The phenol is condensed and catched for recovery. The total residence time of the adduct crystal is 4 hrs in the drying apparatus. Bisphenol A product is dram at a rate of 6.68 Kg/hr, having a phenol content of 30 ppm, a color of 6 APHA (50% alcohol solution), and a purity of greater than 99.95% by weight. The obtained product is sufficient to meet the needs of the raw material for polycarbonate for optical use.

COMPARATIVE EXAMPLE

As described in example 1, the adduct crystal was heated to 130° C. and melted, which was then fed into a package distillation column. The top temperature of the column was 104° C., the bottom temperature of the column was 180° C. The internal pressure of the column was 6,666.1 Pa(50 torr)(abs.). The feed rate was 5 kg/hr. Bisphenol A containing 3% by weight of phenol and traces of other impurities was obtained from the bottom of the column, which was then fed into a falling film dephenolizing device. The operating conditions of the dephenolizing device were as follows: the feed temperature was 180° C., the top temperature was 140° C., the bottom temperature was 224° C., the pressure was 666.61 Pa(5 torr)(abs.). The product bisphenol A was obtained at the rate of 3.20 kg/hr. from the bottom of the dephenolizing device. The product had a purity of greater than 99.9% by weight, a phenol content of less than 20 ppm, and a hazen color of 10 APHA.

We claim:

1. A process for the production of high-quality polycarbonate grade bisphenol A by removing phenol from an adduct crystal of phenol with bisphenol A comprising the steps of directly feeding the adduct crystal of phenol with bisphenol A into a vacuum or pneumatic dephenolizing device under a vacuum or in an inert gas stream, controlling the temperature of the adduct crystal below its melting point, and decomposing the adduct crystal to a gas phase and a solid phase, wherein phenol which is removed from the dephenolizing device by the vacuum or inert gas stream is condensed for recovery and is reused, and wherein solid phase high-quality polycarbonate grade bisphenol A is obtained directly from the dephenolizing device.

2. The process according to claim 1 wherein the inert gas stream comprises any gas which is unreactive to bisphenol A and phenol as well as the adduct crystal thereof.

3. The process according to claim 1 wherein the inert gas stream comprises at least one of nitrogen and argon.

4. The process according to claim 1 wherein the temperature of the adduct crystal is from 40° to 130° C.

5. The process according to claim 1 wherein the operating pressure for vacuum dephenolization is from 266.644 to 6,666.1 Pa (2–50 torr) and the residence time of the adduct crystal is from 1 to 4 hours.

6. The process according to claim 1 wherein the operating condition for inert gas stream dephenolization comprises a residence time from 1 to 3.5 hours and a flow rate of the inert gas stream of from 0.1 to 0.50 m/sec.

7. The process according to claim 1 wherein the process comprises one of a batch operation and a continuous operation.

8. The process according to claim 1 wherein the process comprises a batch operation and the temperature of the adduct crystal is raised from 40° to 130° C. during the batch operation.

9. The process according to claim 1 wherein the process comprises a continuous operation and the adduct crystal is divided into at least two sections of different temperatures during the continuous operation.

10. The process according to claim 1 wherein the adduct is dephenolized in a static or fluid state.

11. The process according to claim 1 wherein heaters are installed inside the dephenolizing device.

* * * * *